(12) United States Patent
Weber et al.

(10) Patent No.: US 7,343,659 B2
(45) Date of Patent: Mar. 18, 2008

(54) METHOD OF MAKING A MEDICAL DEVICE

(75) Inventors: Jan Weber, Maple Grove, MN (US);
Raed Rizq, Fridley, MN (US);
Fernando DiCaprio, St. Paul, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 657 days.

(21) Appl. No.: 10/192,253

(22) Filed: Jul. 10, 2002

(65) Prior Publication Data
US 2004/0010304 A1 Jan. 15, 2004

(51) Int. Cl.
*B23P 17/00* (2006.01)
*A61F 2/06* (2006.01)

(52) U.S. Cl. .................. 29/419.2; 29/516; 29/517; 623/1.34; 604/103.1

(58) Field of Classification Search .......... 29/419.2, 29/516, 517; 72/56; 623/1.11, 1.18, 1.12, 623/1.13, 1.19, 1.2, 1.34, 1.42, 12; 604/103.1
See application file for complete search history.

(56) References Cited

U.S. PATENT DOCUMENTS

| | | | |
|---|---|---|---|
| 3,654,787 A | | 4/1972 | Brower |
| 4,170,887 A | | 10/1979 | Baranov |
| 4,531,393 A | | 7/1985 | Weir |
| 4,863,460 A | * | 9/1989 | Magladry .................. 623/2.39 |
| 4,957,669 A | * | 9/1990 | Primm ........................ 264/443 |
| 4,964,853 A | * | 10/1990 | Sugiyama et al. ...... 604/103.14 |
| 5,089,006 A | | 2/1992 | Stiles |
| 5,442,846 A | | 8/1995 | Snaper |
| 5,485,667 A | * | 1/1996 | Kleshinski ................... 29/447 |
| 5,658,251 A | | 8/1997 | Ressemann et al. |
| 5,674,241 A | * | 10/1997 | Bley et al. .................... 623/1.2 |
| 5,716,410 A | | 2/1998 | Wang et al. |
| 5,720,724 A | | 2/1998 | Ressemann et al. |
| 5,779,731 A | * | 7/1998 | Leavitt ......................... 606/194 |
| 5,824,998 A | | 10/1998 | Livshiz et al. |
| 5,968,052 A | | 10/1999 | Sullivan, III et al. |
| 5,972,027 A | | 10/1999 | Johnson |
| 5,992,000 A | | 11/1999 | Humphrey et al. |
| 6,004,291 A | | 12/1999 | Ressemann et al. |
| 6,036,697 A | * | 3/2000 | DiCaprio ..................... 606/108 |
| 6,096,056 A | | 8/2000 | Brown |
| 6,108,886 A | | 8/2000 | Kimes et al. |
| 6,123,712 A | | 9/2000 | DiCaprio et al. |
| 6,153,252 A | * | 11/2000 | Hossainy et al. ............ 427/2.3 |
| 6,159,227 A | | 12/2000 | DiCaprio et al. |
| 6,174,329 B1 | | 1/2001 | Callol et al. |
| 6,179,811 B1 | * | 1/2001 | Fugoso et al. ........... 604/96.01 |
| 6,229,125 B1 | | 5/2001 | Livshiz et al. |
| 6,231,600 B1 | | 5/2001 | Zhong |

(Continued)

OTHER PUBLICATIONS

Michael M. Plum, "Electromagnetic Forming", 1995, Metals Handbook, vol. 14, 9th edition, ASM, pp. 645-653.*

(Continued)

*Primary Examiner*—Jermie E. Cozart
(74) *Attorney, Agent, or Firm*—Fish & Richardson P.C.

(57) ABSTRACT

A method of making a medical device includes compressing a prosthesis, e.g., a therapeutic agent-carrying stent or stent-graft, to a catheter without contacting an outer surface of the prosthesis, e.g., by electromagnetically compressing the prosthesis.

6 Claims, 4 Drawing Sheets

U.S. PATENT DOCUMENTS

| | | |
|---|---|---|
| 6,240,615 B1 | 6/2001 | Kimes et al. |
| 6,248,129 B1 * | 6/2001 | Froix ......................... 623/1.42 |
| 6,277,110 B1 | 8/2001 | Morales |
| 6,280,412 B1 | 8/2001 | Pederson, Jr. et al. |
| 6,352,547 B1 | 3/2002 | Brown et al. |
| 6,520,934 B1 * | 2/2003 | Lee et al. ................. 604/103.1 |
| 6,585,759 B1 * | 7/2003 | Baum et al. ............... 623/1.18 |
| 2003/0163187 A1 * | 8/2003 | Weber ......................... 623/1.2 |

OTHER PUBLICATIONS

"Magnetic Field and Force Calculations for Magnetic Aided Machining".

Invitation to Pay Additional Fees from PCT/US 03/21526.

* cited by examiner

METHOD OF MAKING A MEDICAL DEVICE

TECHNICAL FIELD

This invention relates to medical devices, such as endoprostheses, and methods of making the same.

BACKGROUND

The body includes various passageways such as arteries, other blood vessels, and other body lumens. These passageways sometimes become occluded or weakened. For example, the passageways can be occluded by a tumor, restricted by plaque, or weakened by an aneurysm. When this occurs, the passageway can be reopened or reinforced, or even replaced, with a medical endoprosthesis. An endoprosthesis is typically a tubular member that is placed in a lumen in the body. Examples of endoprosthesis include stents and covered stents, sometimes called "stent-grafts".

Endoprostheses can be delivered inside the body by a catheter that supports an endoprosthesis in a compacted or reduced-size form as the endoprosthesis is transported to a desired site. Upon reaching the site, the endoprosthesis is expanded, for example, so that it can contact the walls of the lumen.

The expansion mechanism may include forcing the endoprosthesis to expand radially. For example, the expansion mechanism can include the catheter carrying a balloon, which carries a balloon expandable endoprosthesis. The balloon can be inflated to deform and to fix the expanded endoprosthesis at a predetermined position in contact with the lumen wall. The balloon can then be deflated, and the catheter withdrawn.

In another technique, a self-expandable endoprosthesis is formed of an elastic material that can be reversibly compacted and expanded. During introduction into the body, the endoprosthesis is restrained in a compacted condition on a catheter. Upon reaching the desired implantation site, the restraint is removed, for example, by retracting a restraining device such as an outer sheath, enabling the endoprosthesis to self-expand by its own internal elastic restoring force.

During delivery, an endoprosthesis is typically attached to a catheter to prevent the endoprosthesis from slipping off or shifting on the catheter, which can cause loss of the endoprosthesis, and/or inaccurate and imprecise delivery of the prosthesis. Attachment of the endoprosthesis can include mechanically clamping or crimping the endoprosthesis on the catheter.

SUMMARY

This invention relates to medical devices, such as endoprostheses, and methods of making the same.

In one aspect, the invention features a method of making a medical device including securing an endoprosthesis to a support, such as a catheter, without mechanically contacting an outer surface of the endoprosthesis. Securing the endoprosthesis may include compressing the endoprosthesis. Examples of other supports include balloons, guidewires, and sheath introducers.

In another aspect, the invention features a method of making a medical device including electromagnetically compressing a prosthesis to a catheter.

In another aspect, the invention features a method of making a medical device including positioning a prosthesis including a therapeutic agent on an expandable portion of a catheter, and electromagnetically compressing the prosthesis.

Embodiments of the aspects of the invention may include one or more of the following features. The method includes electromagnetically compressing the prosthesis on an inflatable balloon on the catheter. The method includes heating the expandable portion or the balloon. The method includes positioning a restraining device over the compressed prosthesis. The method includes compressing, e.g., electromagnetically, different portions of the prosthesis with different forces. The method further includes supporting the prosthesis on the catheter. The method further includes axially and/or radially translating the prosthesis. The method further includes positioning a mandrel in the catheter.

The prosthesis can be a balloon-expandable stent, a balloon-expandable stent-graft, a self-expandable stent, a self-expandable stent-graft, or combinations thereof. The prosthesis can include a therapeutic agent.

In another aspect, the invention features medical devices made according to the methods described herein.

In another aspect, the invention features a method of making a medical device including securing a medical balloon to a catheter, and subsequently securing a marker band under the balloon to the catheter.

Embodiments may include one or more of the following features. The band is secured to the catheter without mechanically contacting the band. The band is secured to the catheter electromagnetically. The band is visible by magnetic resonance imaging. The band is formed of a material having dysprosium or gadolinium. The band is formed of a material selected from the group consisting of gold, platinum, tungsten, and tantalum.

In another aspect, the invention features a method of making a medical device including securing a marker band to a support without contacting an outer surface of the band. The support can be, e.g., a catheter, a medical balloon, a guidewire, or a stent.

In another aspect, the invention features a method including providing an endoprosthesis including a metal body and a polymer layer, and reducing the size of the endoprosthesis without contacting the endoprosthesis. The polymer layer may include a drug. The polymer layer may be on an outside surface of the metal body. The endoprosthesis, for example, a stent, can be reduced in size without contacting the polymer layer. The method can further include securing the endoprosthesis to a support, e.g., a catheter or a medical balloon.

Embodiments may have one or more of the following advantages. An endoprosthesis can be attached, e.g., crimped, to a catheter without contacting an exterior of the endoprosthesis. Not contacting the exterior of the prosthesis can reduce damage to the prosthesis, for example, due to relatively high shearing forces normal to and/or tangential to the surface of the prosthesis. Reducing shearing forces can be particularly advantageous for prostheses carrying a drug, such as drug-coated stents and stent-grafts in which the drug, e.g., a shear-sensitive material, such as DNA or RNA, is applied to a surface or is embedded in a matrix, e.g., polymer matrix, applied to the prosthesis. Not contacting the exterior of the prosthesis can also reduce cross contamination between prostheses, and/or between a prosthesis and a conventional crimper.

As described herein, in embodiments in which the prosthesis is self-expandable, the methods can allow portions of the prosthesis already loaded in a restraining device, e.g., a sheath, to be compressed. This may allow unloaded portions of the prosthesis to be loaded into the restraining device without the inner wall of the restraining device rubbing against the exterior surface of the loaded portions of the prosthesis. As a result, damage to the surface of the prosthesis is reduced.

The methods can be relatively quick and reproducible, with good accuracy and precision. For example, compression forces, which can be proportional to the square of a discharge current, can be accurately and precisely controlled by controlling the discharge current. In some embodiments, the prosthesis can be quickly and permanently deformed without the prosthesis substantially springing back. The methods can be used to compress or to crimp prostheses with various diameters.

Other features and advantages of the invention will be apparent from the description of the preferred embodiments thereof and from the claims.

DETAILED DESCRIPTION OF THE PREFERRED EMBODIMENTS

Figure 1:
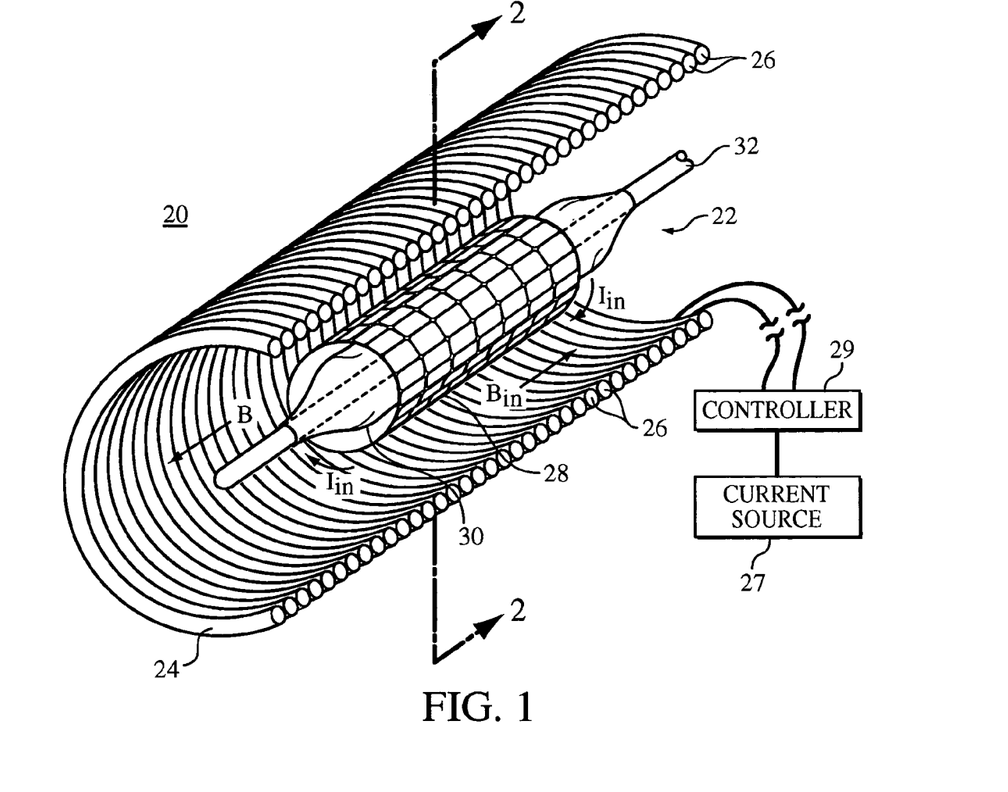
FIG. 1 is a partially cut-away, perspective view of an embodiment of a system for making a medical device.
Figure 2:
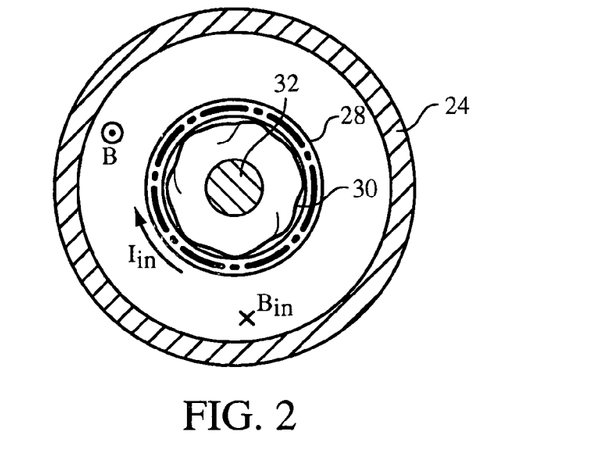
FIG. 2 is a cross-sectional view of the system of FIG. 1, taken along line 2-2.

FIGS. 1 and 2 show a system 20 for making a medical device 22. In the embodiment illustrated, a prosthesis 28, such as a stent or a stent-graft, is secured, e.g., crimped, to a balloon 30 of a catheter 32 using electromagnetic forces. During securement of prosthesis 28 to catheter 32, the outer surfaces of the prosthesis experience no physical contact or shear forces. As a result, contamination of or damage to medical device 22, particularly to prosthesis 28, is minimized.

System 20 includes a tube 24 formed of wound wire 26. The ends of wire 26 are connected to a current source 27. Current source 27 can be a power supply of constant or variable current controlled by a controller 29, which may include a capacitor bank and appropriate switches.

Referring particularly to FIG. 1, prosthesis 28, is uncompressed, e.g., as formed, or partially compressed, and is positioned over balloon 30. For example, prosthesis 28 can be centered on balloon 30. Balloon 30 is not fully inflated, i.e., the balloon can be partially or completely deflated. To secure prosthesis 28 to balloon 30 and catheter 32, a current is discharged through wire 26 of tube 24. The discharged current generates a rapidly changing magnetic flux that penetrates electrically conductive material in prosthesis 28, e.g., the stainless steel of a stent. Consequently, an eddy current is induced in prosthesis 28. This induced current has an associated induced magnetic field that has a polarity that opposes the polarity of the magnetic field of tube 24. Referring as well to FIG. 2, as a result, magnetic repulsion between (stationary) tube 24 and prosthesis 28 forces the prosthesis radially inward to attach, e.g., by crimping, the prosthesis to the balloon 30 and catheter 32.

Repulsive magnetic forces are generated between a forming coil (e.g., tube 24) and a work piece positioned inside the forming coil (e.g., prosthesis 28) to perform mechanical work, according to "Lenz's Law of Repulsion". In operation, a rapidly changing, unidirectional current is applied to the forming coil to generate a rapidly changing magnetic flux. The relatively high rate of change of flux can be produced, for example, by rapidly discharging a relatively large electric charge from an energy storage capacitor through a low resistance coil. As a result, this large current causes a rapidly changing magnetic flux (e.g., arrow B, FIGS. 1 and 2). When a rapidly changing magnetic flux penetrates an electrically conductive material, a similarly changing current, e.g., eddy current, is induced in the material (e.g., arrow $I_{in}$, FIGS. 1 and 2). The induced current can be proportional to the initial intensity and time rate of change of the magnetic flux. That is, the higher the rate of change, the greater the induced current.

The induced current has an associated induced magnetic field (e.g., arrow $B_{in}$, FIGS. 1 and 2). According to Lenz's Law, the induced magnetic field must oppose the change in flux from the forming coil. Here, the induced magnetic field ($B_{in}$) has a polarity opposite the polarity of the magnetic field (B) inducing the current. Also, the magnetic flux from the induced current is directed radially outward from the work piece against the magnetic flux of the forming coil. As a result, magnetic repulsion between the work piece and the forming coil can force the work piece radially inward, i.e., compress the work piece.

The force generated between the forming coil and the work piece can be controlled by controlling the applied current and/or the distance between the coil and the work piece. For example, in some embodiments, the force is proportional to the square of the discharge current, i.e., the higher the discharge current, the greater the magnetic force. The force can also be inversely proportional to a separation distance between the forming coil and the work piece, i.e., the closer the work piece is from the forming coil, the more force the work piece can experience.

The current-to-compression relationship and/or the separation distance-to-compression relationship for controllably compressing a work piece can be determined empirically, such as by observing the degree of deformation in the work piece as a function of applied current and/or distance between the work piece and forming coil. For example, a pulse of current can be applied, and the change, e.g., decrease, in the diameter of the work piece can be measured as a function of the applied current and/or the distance between the work piece and forming coil. The degree to which the work piece displaces can be measured, for example, by using an optical fiber pass through the forming coil. During fabrication, this data can be used to apply a predetermined current based on the size of the work piece, e.g., the separation distance, and the degree of compression desired. As a result, using magnetic forces to deform a work piece can provide reproducibly accurate results. The degree of compression can also be a function of the endoprosthesis material, e.g., stainless steel, which can also be determined empirically.

Compression of the work piece can be performed in one step or as a series of steps. For example, using predetermined data, the work piece can be compressed from a starting dimension to a final dimension in one step by applying a sufficient large current. Alternatively, the work piece can be sequentially compressed by applying a series of current pulses, each sufficient to compress the work piece until the desired size is achieved. Each current pulse can be adjusted to provide the desired compression using the predetermined data relating to compression as a function of current, separation distance, and/or endoprosthesis material.

The use of magnetic forces to deform a work piece is a technique known as "magnetic pulse forming", which is described, for example, in Batygin Yu et al., "The Experimental Investigations of the Magnetic Pulse Method Possibilities for Thin-walled Metal Plates Deformation", Technical Electro-dynamics, 1990, #5, p. 15-19, hereby incorporated by reference.

Medical device 22 includes prosthesis 28 and inflatable balloon 30 attached to catheter 32. Prosthesis 28, balloon 30 and catheter 32 can be conventional. For example, prosthesis 28 can be a conventional stent or a conventional stent-graft. The stent can be made of an electrically conducting material such as Nitinol or Elgiloy™ stainless steel. The stent-graft can be a stent attached to a biocompatible, non-porous or semi-porous polymer matrix made of polytetrafluoroethylene (PTFE), expanded PTFE, polyethylene, urethane, or polypropylene. Prosthesis 28 can be balloon expandable, self-expandable, or a combination of both. Examples of prosthesis 28 are described in U.S. Pat. Nos. 5,725,570 and 5,234,457, all hereby incorporated by reference. Prosthesis 28 can include a releasable therapeutic agent or a pharmaceutically active compound, such as described in U.S. Pat. No. 5,674,242, and commonly-assigned U.S. Ser. No. 09/895,415, filed Jul. 2, 2001, all hereby incorporated by reference. The therapeutic agents or pharmaceutically active compounds can include, for example, anti-thrombogenic agents, antioxidants, anti-inflammatory agents, anesthetic agents, anti-coagulants, and antibiotics. Device 22 can also include side ports adapted for perfusion.

In some embodiments, catheter 32 can be fitted with a mandrel, e.g., a hypotube, placed inside the catheter. The mandrel, which can act as a die about which the prosthesis is deformed, can limit the degree to which the prosthesis is compressed, e.g., so that the prosthesis does not become overly compressed. The mandrel can include wire coiled about its axial axis to generate repulsive magnetic forces from within the catheter or the prosthesis. The magnetic forces can be used to force the prosthesis radially outward.

Figure 3:
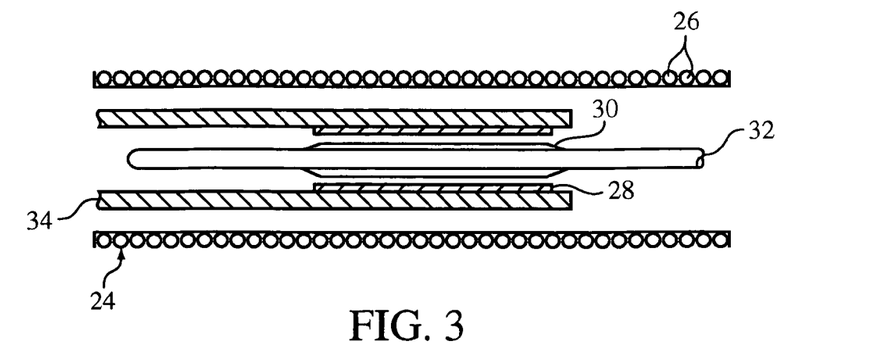
FIG. 3 is a cross-sectional, schematic view of an embodiment of a system for making a medical device.

Referring to FIG. 3, in some embodiments, prosthesis 28 can be positioned over balloon 30 using a temporary sheath 34 prior to compression. Sheath 34 can be used as a centering device. Sheath 34, for example, an electrically non-conducting tube such as a polymer or glass tube, has an inner diameter larger than the outer diameter of prosthesis 28. For example, the sheath can have a diameter sufficiently large to load the prosthesis into the sheath without subjecting the prosthesis to damaging shear forces. After prosthesis 28 is loaded in sheath 34, the sheath is positioned such that the prosthesis is positioned over balloon 30, which can be partially or fully compressed. Prosthesis 28 can be compressed and secured to balloon 30 as described above, and sheath 34 can then be withdrawn from tube 24. In embodiments, sheath 34 contacts only selected portions of prosthesis 28, e.g., the proximal and/or distal end of the prosthesis. In embodiments, sheath 34 can serve as a field shaper. Sheath 34 can be made of a material and/or has a configuration that enhances the electromagnetic field.

Figure 4:
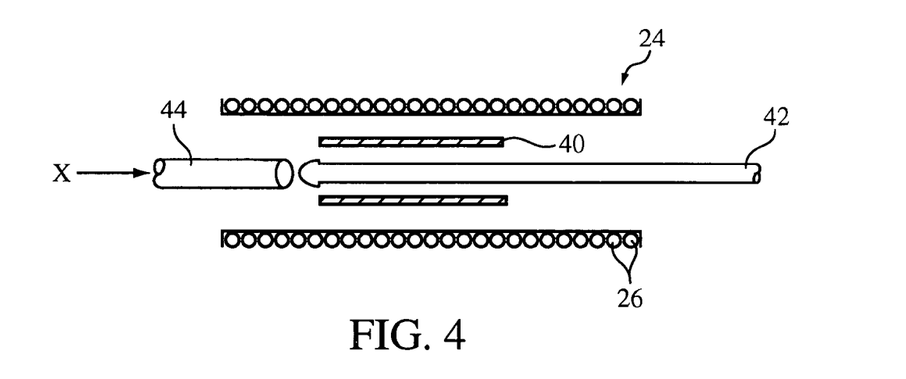
FIG. 4 is a cross-sectional, schematic view of an embodiment of a system for making a medical device.

Magnetic pulse forming can also be used to secure self-expanding prostheses to a catheter. Referring to FIG. 4, a self-expandable prosthesis 40 is positioned over a predetermined portion of a catheter 42, e.g., near the distal end of the catheter. Prosthesis 40 and catheter 42 can be conventional devices used with self-expanding stents and stent-grafts. In some embodiments, catheter 42 can be fitted with a mandrel, as described above.

During fabrication, prosthesis 40 is magnetically compressed to catheter 42, as described above. When prosthesis 40 is compressed to a predetermined size, a restraining device 44, e.g., an outer sheath, is moved over the prosthesis (arrow X) to hold the prosthesis in a compressed state. In some embodiments, the applied current is sufficiently varied to provide a changing magnetic flux to keep the prosthesis sufficiently compressed so that the restraining device can be moved into place over the prosthesis.

Figure 5A:
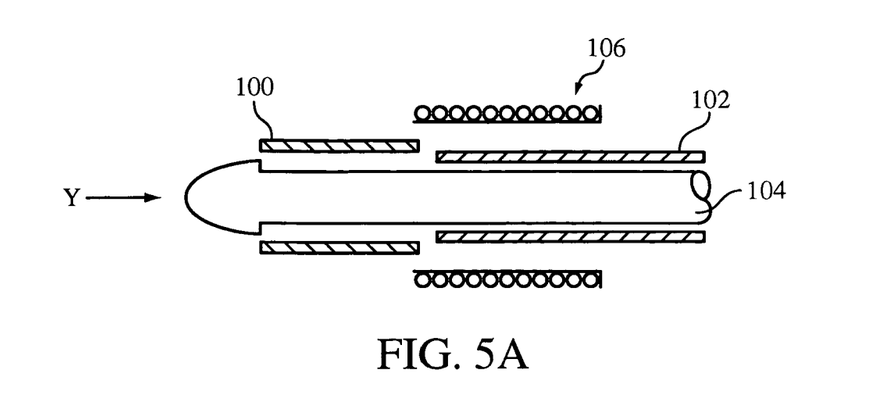
FIGS. 5A, 5B, and 5C are schematic views of an embodiment of a method for making a medical device.
Figure 5B:
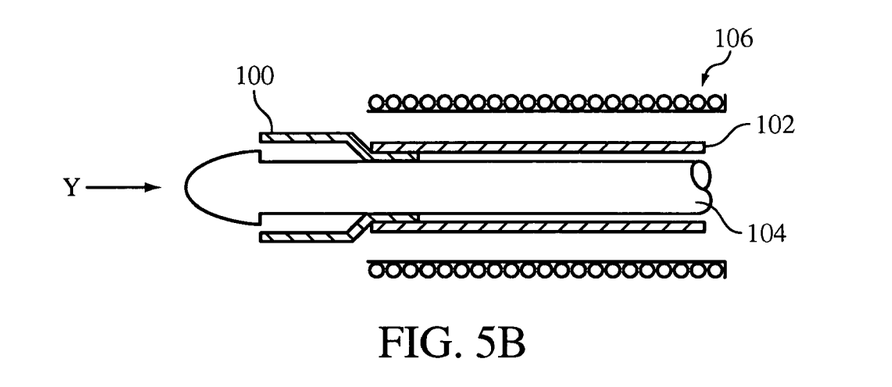
Figure 5C:
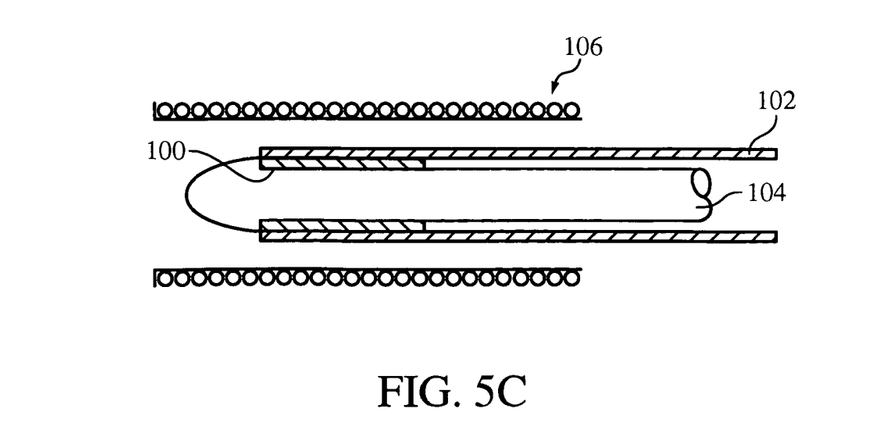

In embodiments, a prosthesis can be compressed sequentially along its axial axis, and a sheath can be sequentially positioned over compressed portions of the prosthesis. Referring to FIGS. 5A-5C, a prosthesis 100 and a restraining device 102, e.g., a polymer sheath, are positioned over a catheter 104 (FIG. 5A). A portion of prosthesis 100, e.g., the proximal end, can then be compressed. For example, prosthesis 100, device 102, and catheter 104 can be introduced incrementally into tube 106 and moved proximally (arrow Y). As portions of prosthesis 100 experience a magnetic flux from tube 106 and compress, restraining device 102 can be slid over the compressed portions (FIG. 5B). This process of compressing increasingly longer portions prosthesis 100 and sliding restraining device 104 over the compressed portions continues until the restraining device covers prosthesis 100 (FIG. 5C). This process takes advantage of the property of a magnetic flux to penetrate electrically non-conducting materials, e.g., a polymer restraining device, and to selectively interact with electrically conducting materials. As a result, an electrically conducting prosthesis can be loaded into an electrically non-conducting restraining device without exposing the prosthesis to damaging shear forces, even when portions of the prosthesis is inside the restraining device.

Other methods of selectively compressing different portions of prosthesis 100 include modifying tube 106 to include different diameters, coil densities, or independently-operable coil sections, as described below.

Figure 6:
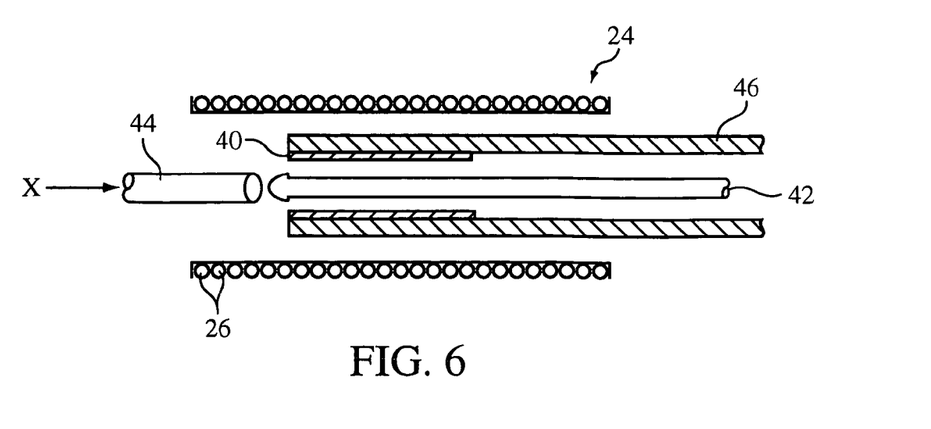
FIG. 6 is a cross-sectional, schematic view of an embodiment of a system for making a medical device.

Referring to FIG. 6, in certain embodiments, self-expanding prosthesis 40 can be compressed on catheter 42 using a temporary sheath 46 prior to compression. Sheath 46 is generally the same as sheath 34 described above and can be used in a similar manner.

Other Embodiments

In certain embodiments, the forming coil, e.g., tube 24, can be modified to provide enhanced control of the magnetic fluxes and, as a result, the forces that are generated. Modifying the forming coil can be useful where it is desirable to apply non-uniform forces along the axial axis. For example, some prostheses may be formed of different materials, and the materials may require different forces for compression. Some prostheses may be formed with portions of different structures, e.g., a combination of self-expandable and balloon-expandable portions, and the portions may require different forces for compression. Examples are described in Andersen, U.S. Pat. No. 5,366,504, hereby incorporated by reference.

Figure 7:
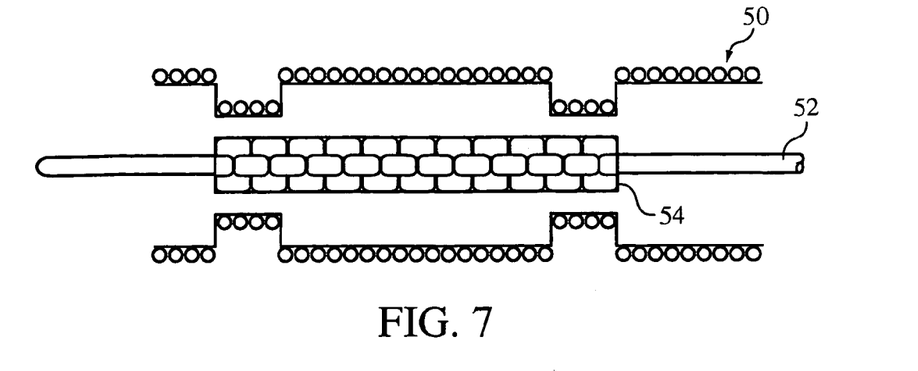
FIG. 7 is a cross-sectional, schematic view of an embodiment of a system for making a medical device.

In some embodiments, the forming coil can be modified to have a non-uniform inner diameter. That is, the forming coil can have portions with different diameters. The portions with different diameters can vary step-wise (FIG. 7). Alternatively or in addition, portions with different diameters can vary as a taper, relatively gradually or suddenly. Since the force can be inversely proportional to the distance between the forming coil and the work piece, portions of the work piece closer to the forming coil experience more force than portions relatively farther away from the forming coil, for otherwise substantially identical conditions. Catheter 52 and prosthesis 54 can be conventional, such as those used in balloon-expandable or self-expandable devices. Portions of the prosthesis requiring greater compression forces are positioned relatively closer to the forming coil.

Figure 8:
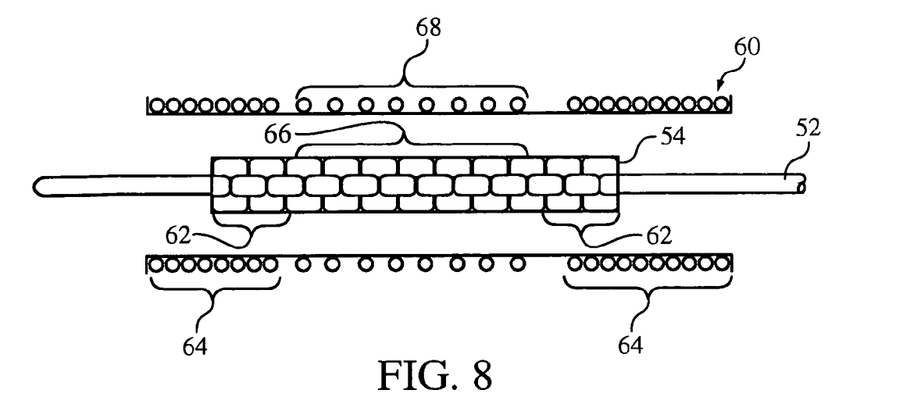
FIG. 8 is a cross-sectional, schematic view of an embodiment of a system for making a medical device.

Alternatively or in addition, the forming coil can be modified to have a varying number of wire coils per unit distance. Generally, for otherwise substantially identical conditions, the higher the number of wire coils per unit distance, the greater the magnetic force generated per given pulse of current. For example, referring to FIG. 8, portions 62 of prosthesis 54 requiring relatively high compression forces can be aligned with portions 64 of tube 60 having a relatively high number of wire coils per unit distance. Portions 66 of prosthesis 54 requiring relatively low compression forces can be aligned with portions 68 of tube 60 having a relatively low number of wire coils per unit distance.

Alternatively or in addition, the forming coil can be formed, along its axial length, of independently operable sections of wire coils connected to independently controllable current sources. The amount of magnetic flux and compression forces generated can be controlled by applying predetermined current pulses to predetermined sections of wire coils. Relatively high current pulses are applied to sections where relatively high compression forces are wanted.

In some embodiments, the current induced in the work piece, e.g., the prosthesis, can increase the temperature of the work piece. This heat can affect securement of the prosthesis to the balloon, for example, by softening the balloon such that the bond between the prosthesis and the balloon can be enhanced. Alternatively or in addition, the balloon and/or the catheter can be heated, e.g., using infrared radiation or a heatable mandrel. In embodiments, low current pulses can be applied to the forming coil. For example, low current pulses can be applied, e.g., alternating with high current pulses, to heat the endoprosthesis to further embed the endoprosthesis into the balloon.

The forming coil may have non-circular cross sections, e.g., elliptical, oval, or polygonal having three, four, five, six, or more sides that can be equal or unequal.

The medical devices described above can include radiopaque markers to help the user position the devices. For example, the wire of the stent or stent-graft can be radiopaque, e.g., by including gold or tantalum.

Magnetic pulse forming can also be used to attach band(s) (e.g., marker bands that are radiopaque or magnetopaque, i.e., visible by magnetic resonance imaging (MRI)) to various supports. Examples of supports include catheters, balloons, guidewires, sheath introducers, temporary filters (e.g., non-metallic, such as ceramic or polymeric, filters), stents, and grafts. In some embodiments, the band(s) can be placed on the support, e.g., slipped-fit around a polymer shaft, and the band(s) can be attached in a forming coil as described herein. Suitable materials for the bands include, for example, gold, platinum, tungsten, tantalum, and metal alloys containing a sufficient percentage of heavy elements. Suitable magnetopaque materials include, for example, non-ferrous metal-alloys containing paramagnetic elements (e.g., dysprosium or gadolinium) such as terbium-dysprosium, dysprosium, and gadolinium; non-ferrous metallic bands coated with an oxide or a carbide layer of dysprosium or gadolinium (e.g., $Dy_2O_3$ or $Gd_2O_3$); non-ferrous metals (e.g., copper, silver, platinum, or gold) coated with a layer of superparamagnetic material, such as nanocrystalline $Fe_3O_4$, $CoFe_2O_4$, $MnFe_2O_4$, or $MgFe_2O_4$; and nanocrystalline particles of the transition metal oxides (e.g., oxides of Fe, Co, Ni).

Magnetic pulse forming can be particularly useful for attaching marker bands to an inner shaft of a balloon catheter (i.e., underneath a balloon), after the balloon has been attached (e.g., welded) to the inner shaft and an outer shaft. Marker bands are typically attached to the inner shaft, e.g., at an axial position corresponding to the transition between the balloon and the balloon cone, by a swaging process before the balloon is attached to the catheter. With this method, however, it can be difficult to adjust the positions of the marker bands after they are attached, e.g., to compensate for balloons of different lengths. Using non-contact crimping, the marker bands can be secured in place relative to the balloon after the balloon has been attached.

Numerous methods can be used. For example, to move the marker bands axially along the inner shaft underneath the balloon, (a) inflate the balloon at low pressure, if necessary; (b) determine the position of the marker band(s) from the desired final position(s); and (c) grip the marker band(s) with soft mini-grippers (the balloon can be squeezed at low pressures) and incrementally slide the band(s) along the inner shaft to the final position; (d) position the balloon with the marker band(s) in place within the magnetic pulsing system, inflate the balloon to center the bands in the middle of the coil, and non-contact crimp the band(s) to the inner shaft; and (e) repeat any step(s) as necessary. In other embodiments, the band(s) can be moved along the inner shaft by inserting a polymer wire, or another manipulating device, through a lumen of the catheter, and pushing the marker band(s) (preferably positioned proximally) in position. In other embodiments, the band(s) can be moved along the inner shaft by positioning the balloon such that the marker band(s) is outside the forming coil, and by pulsing the coil. The magnetic field from the coil can axially displace (e.g., attract or repel) the marker band(s). The marker band(s) can also be axially displaced by using permanent magnets and/or electrostatic forces.

Other electrically conducting medical devices can also be formed by magnetic pulse forming. For example, electrically conducting guidewires having non-linear portions, e.g., curved tips, can be formed by selectively deforming the axial length of a guidewire about a mandrel or a mold having a predetermined profile. In embodiments, the forming coil can be modified to include selected diameters, coil densities, and/or independently operable coil sections, as described herein.

Magnetic pulse can also be used to deform electrically non-conductive devices, e.g., a polymer tube or a PTFE stent or stent-graft. For example, to attach a polymer tube to a catheter, the catheter can be placed inside the polymer tube. The catheter and the polymer tube can then be placed inside an electrically conductive member, such as a metal tube or an electrically conducting self-expanding stent. Using magnetic pulse forming, the electrically conductive member can be deformed to deform, e.g., compress, the polymer tube to the catheter. In embodiments where the electrically conductive member is a self-expandable member, the member can then expand by its internal elastic forces and be removed. The electrically conductive member and/or the non-conductive device can be coated, e.g., with PTFE, to prevent sticking between the member and the device. Alternatively, or in addition, a forming coil can be placed inside the catheter to force the electrically conductive member radially outward using magnetic pulse forming. The forming coil can also serve as a mandrel to limit the degree of deformation, as described above.

Magnetic pulse forming can be used with conventional crimping methods. For example, a prosthesis can be partially compressed using mechanical crimpers, positioned over a catheter, and then further compressed using magnetic pulse forming.

During operation, the prosthesis can be moved within the forming coil, e.g., vibrated axially and/or radially, to provide varying eddy currents and magnetic forces, which can enhance, e.g., make more uniform, compression. Alternatively or in addition, the applied current can be controlled, e.g., variably, to provide different radial compression forces.

In embodiments, a coil of wire can be placed in a catheter to expand an endoprosthesis, e.g., in a body lumen.

The following example is illustrative and not intended to be limiting.

EXAMPLE

Figure 9:
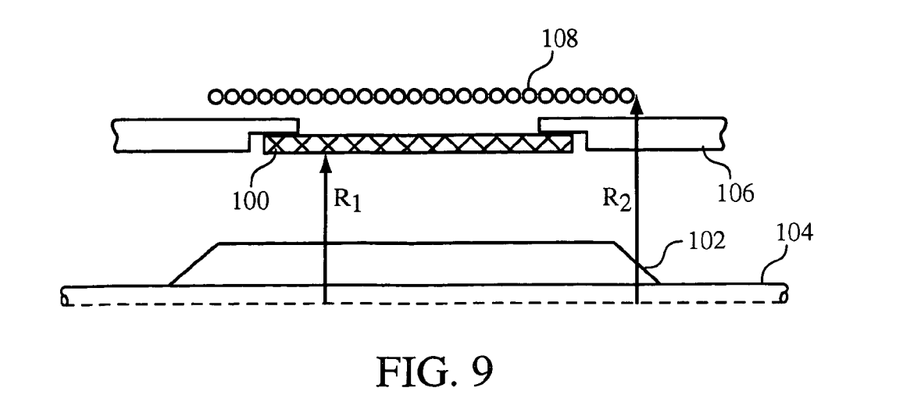
FIG. 9 is a schematic diagram of an embodiment of a system for making a medical device.

Referring to FIG. 9, a stent $100$ held by a glass tube $106$ is centered over a balloon $102$ of a catheter $104$. Stent $100$, tube $106$, and catheter $104$ are positioned inside a forming coil $108$. Balloon $102$ and catheter $104$ can be centered in coil $108$ using a ceramic mandrel (not shown). Stent $100$, e.g., an Express stent available from Boston Scientific Corp., has a length of 8 mm and a starting (uncompressed) radius, $R_1$, of 2 mm, and coil $108$ has a radius, $R_2$, of 2.1 mm.

Considering the actual outer surface and open areas of stent $100$, it is believed that a final pressure of 34 N/mm$^2$ is used to crimp the stent to a final radius of 0.5 mm. This pressure is used in the last 0.1 mm reduction in radius, when stent $100$ contacts balloon $102$. Before stent $100$ contacts balloon $102$, the force used to deform the stent from a radius of 2 mm to 0.6 mm is believed to be less than 3 N. The surface area of stent $100$ (8.79 mm$^2$) during compression remains relatively the same since the open areas of the stent decrease during compression. Accordingly, the amount of energy required to crimp is pAd=[(0.2·34)+(1.4·3)]×8.79=97 N·mm=0.097 Joule.

As described herein, when a current is generated in forming coil $108$, a current is induced in stent $100$, which generates a magnetic field opposing the magnetic field of the coil. Here, assuming the diameter and surface area of coil $108$ and stent $100$ are nearly equal, the current in the stent is nearly equal to the current in the coil at t=0.

According to the laws of Biot Savard, two parallel wires of length L carrying a current $I_1$ and $I_2$ and separated by a distance r experience a force $F=(I_1 I_2 L^2 10^{-7})/r^2$. This force can be applied to compress stent $100$, also providing the stent with kinetic energy. As calculated above, the kinetic energy ($\frac{1}{2}$ mv$^2$) required is 0.094 Joule, which means that the initial velocity, v, of stent $100$ is 166 m/s. (The mass of the stent is $6.8 \times 10^{-6}$ kg.) Assuming a design in which a single turn coil is used, i.e., a flat wire as wide as the length of stent $100$, the current $I_1$ through the coil is nearly equal to the current $I_2$ through the stent. The net radial force acting on the stent is $F=10^{-7} I^2 (\pi^2 R_1 R_2)/R_2 - R1)$ $^2$3N. Three Newtons is the elastic force of the stent. The speed of the stent is equal to the integral of the force divided by the mass.

Using numerical solution, and assuming time steps of 10-6 seconds, sending 1500 Amperes through the coil can result in a maximum speed of 152 m/s. Commercial high current pulse generators can deliver up to 2400 Amperes. The current can also be reduced to crimp in steps. For example, a current of 200 Ampere can reduce the radius from 2 mm to 1.54 mm.

At the same time, part of the induced current in stent $100$ can be dissipated into heat by Ohmic losses. The heat dissipation during crimping is $P=I^2 R dt$, where $R=\rho L/A$. Here, $\rho=1.676 \times 10^{-5}$ W cm (for steel), L=0.1257 cm, A=0.008 Cm$^2$ (thickness of stent=0.01 mm, length=0.8 cm), so $R=2.62 \times 10^{-4}$ Ohm. Heat dissipation is 590 Watts. The time period to reach 150 m/s is $5 \times 10^{-6}$ seconds. Therefore, the amount of heat dissipated during this time period is 0.003 Joule, which is relatively small, suggesting that most of the energy can be used to compress the stent.

The above calculations do not, e.g., account for decay of the induced current, but the example provides one illustrative guideline for securing an endoprosthesis to a catheter.

Other embodiments are within the claims.

What is claimed is:

1. A method of making a medical device, the method comprising:
   securing a medical balloon to a catheter; and
   subsequently securing a marker band under the balloon to the catheter.

2. The method of claim 1, wherein the band is secured to the catheter without mechanically contacting the band.

3. The method of claim 1, wherein the band is secured to the catheter electromagnetically.

4. The method of claim 1, wherein the band is visible by magnetic resonance imaging.

5. The method of claim 4, wherein the band is formed of a material having dysprosium or gadolinium.

6. The method of claim 1, wherein the band is formed of a material selected from the group consisting of gold, platinum, tungsten, and tantalum.

* * * * *